US006881588B2

(12) United States Patent
Tegeler et al.

(10) Patent No.: US 6,881,588 B2
(45) Date of Patent: Apr. 19, 2005

(54) FLUID TREATMENT DEVICE

(75) Inventors: Tony J. Tegeler, Bloomington, IN (US); Yehia Mechref, Bloomington, IN (US); Milos V. Novotny, Bloomington, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 152 days.

(21) Appl. No.: 10/277,556

(22) Filed: Oct. 18, 2002

(65) Prior Publication Data

US 2004/0077101 A1 Apr. 22, 2004

(51) Int. Cl.[7] .................................................. H01J 49/04
(52) U.S. Cl. ....................... 436/180; 436/161; 436/173; 436/174; 436/179; 422/70; 422/99; 250/288
(58) Field of Search ................................ 436/161, 173, 436/174, 179, 180; 422/70, 99; 73/61.56, 61.58; 204/450–453; 250/288; 210/198.2, 656

(56) References Cited

U.S. PATENT DOCUMENTS

| 4,740,298 | A | | 4/1988 | Andresen et al. |
| 4,843,243 | A | | 6/1989 | Biemann et al. |
| 4,867,947 | A | | 9/1989 | Andresen et al. |
| 5,580,434 | A | | 12/1996 | Robotti et al. |
| 5,599,718 | A | * | 2/1997 | Gorog .......................... 436/69 |
| 5,633,496 | A | | 5/1997 | Sakairi et al. |
| 6,228,659 | B1 | | 5/2001 | Kowallis et al. |
| 6,287,872 | B1 | | 9/2001 | Schurenberg et al. |
| 6,355,487 | B1 | | 3/2002 | Kowallis |
| 6,414,306 | B1 | | 7/2002 | Mayer-Posner et al. |
| 6,481,648 | B1 | * | 11/2002 | Zimmermann .............. 239/690 |
| 2001/0033809 | A1 | | 10/2001 | Karger et al. |

OTHER PUBLICATIONS

"Molecular Sieve" Chromatography on Polyacrylamide Gels, Prepared According to a Simplified Method, Stellan Hjerten, Archives of Biochemistry and Biophysics, Supplement 1, 147–151 (1962).

* cited by examiner

Primary Examiner—Jan M. Ludlow
(74) Attorney, Agent, or Firm—Barnes & Thornburg LLP

(57) ABSTRACT

A fluid treatment device is disclosed for mixing first and second fluids. The first fluid may be a treatment liquid that is contained in a container and that is used to change a property, such as the pH, density or ionic strength, of the second fluid. In some illustrative embodiments, the fluid treatment device is used to create an effluent by adding a buffer material and/or a matrix material to an analyte for subsequent MALDI MS analysis of the effluent. A mixing space is defined in a container between ends of first and second conduits. In some embodiments, a junction member couples together the ends of the first and second conduits. The junction member has a main passage that receives the ends of the first and second conduits. The junction member has at least one opening that provides fluid communication between an interior region of the container and the mixing space.

52 Claims, 7 Drawing Sheets

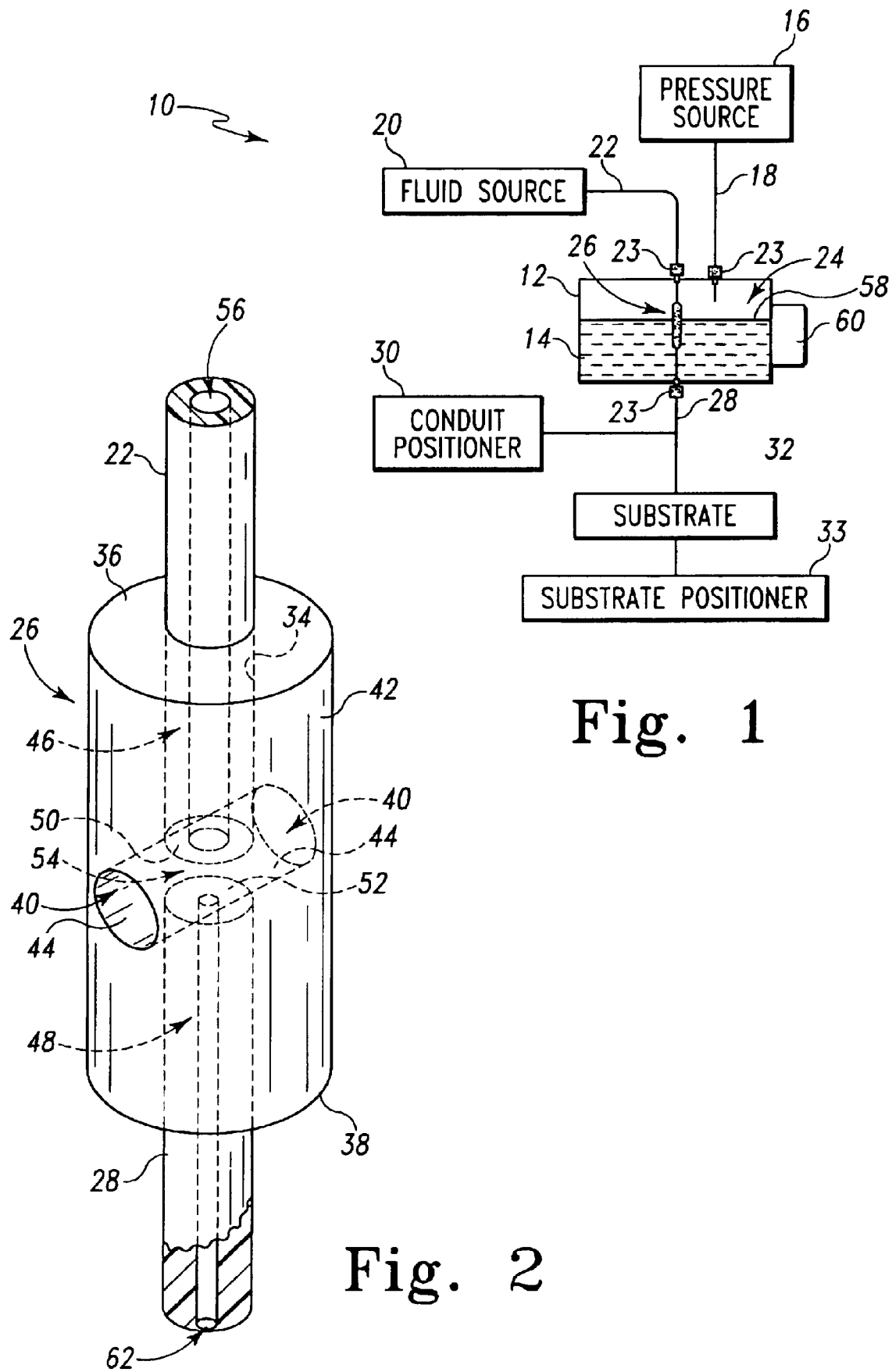

US 6,881,588 B2

FLUID TREATMENT DEVICE

BACKGROUND OF THE INVENTION

The present invention relates to devices for treating fluids, and particularly to fluid treatment devices for mixing first and second fluids. Some embodiments of the present invention relate to fluid treatment devices for mixing matrix materials with fluids carrying analytes so that, after the mixture is placed on substrates, analysis by matrix-assisted laser desorption ionization time-of-flight mass spectrometry (MALDI/TOF/MS) may be performed.

In broad general terms analytical chemistry is concerned with separating, identifying, and quantifying the relative amounts of the chemical components of a sample. Frequently, samples are subjected to a number of successive analytical techniques in order to advance the analysis of the components contained therein. This strategy of utilizing successive analytical techniques can be useful in analyzing any type of chemical component, but it is particularly helpful when the components to be analyzed are biological molecules, such as polypeptides, proteins, lipids, polynucleotides, and/or polysaccharides. For example, it is common to initially subject a sample containing biological molecules to a chromatography technique in order to separate the constituent molecules of the sample into a number of liquid fractions collected from the effluent of the chromatography system (e.g. effluent from electrically driven devices, such as CE and CEC devices, or pump driven devices, such as capillary LC and micro-LC). Thereafter, each fraction can be subjected to a subsequent analytical technique in order to obtain additional information about the biological molecules contained therein. Examples of analytical techniques the fractionated biological molecules can be subjected to include, but are not limited to, infrared spectroscopy, mass spectrometry, and nuclear magnetic resonance.

However, it should be appreciated that prior to analyzing the constituents of a fraction with a subsequent analytical technique, it is frequently desirable to alter the chemical/physical characteristics of the liquid containing the biological molecules of interest. For example, it may be desirable to introduce an additional substance into the liquid containing the molecules of interest to serve as a matrix material for subsequent MALDI mass spectrometry analysis, or the additional substance may be introduced to alter the pH, density, and/or ionic strength of liquid in order to prepare it for further analysis. Accordingly, an apparatus and method for altering the chemical/physical characteristics of a liquid containing a substance of interest is desirable.

SUMMARY OF THE INVENTION

A fluid treatment device in accordance with the present invention comprises one or more of the following features or combinations thereof:

A container is provided for receiving a first fluid, which may include, for example, a treatment liquid, a buffer material, and/or a matrix material. A fluid source is provided for moving a second fluid, such as an analyte, into the container. The fluid source may comprise a separator apparatus, such as a liquid chromatography apparatus, a capillary electrophoresis apparatus, or a capillary electrochromatography apparatus. The separator apparatus may be operable to separate the second fluid into its constituent molecules. A first conduit or delivery conduit may be provided to transport the second fluid into the container. A second conduit or deposition conduit may be provided to transport a mixture of the first and second fluids out of the container. A mixing space may be defined in the container between ends of the first and second conduits. A junction member or connection sleeve may be coupled to the first and second conduits in the container. The junction member or connection sleeve may be provided with a channel or main passage. The ends of the first and second conduits may be situated in the main passage. The main passage may be configured to permit fluid flow between the first and second conduits. The junction member or connection sleeve may have at least one opening providing fluid communication between an interior region of the container and the main passage. The first fluid may move from the interior region into the main passage through the at least one opening. A pressure source, such as a source of pressurized nitrogen, may be provided to pressurize an interior region of the container. The pressure source may be adapted to maintain the first fluid under sufficient pressure to result in movement of the first fluid into the main passage of the junction member through the at least one opening. The pressure source may be adapted to maintain sufficient pressure in the container to move the mixture of the first and second fluids from the main passage of the junction member, through the second conduit, and out of the container.

Thus, a fluid treatment device is provided for mixing first and second fluids. In some embodiments, such a device comprises a container and a junction member situated in the container. The junction member has a main passage. The device further comprises a first conduit having a first end in the main passage and a second end outside the container. In addition, the device comprises a second conduit having a first end in the main passage and a second end outside the container. A mixing space is defined in the main passage between the first end of the first conduit and the first end of the second conduit. The junction member has at least one opening providing fluid communication between an interior region of the container and the mixing space.

In some embodiments, the junction member comprises a tubular connection sleeve that is oriented vertically in the interior region of the container and the container is filled partially with a first fluid, such as a matrix material, by a sufficient amount to permit the first fluid to flow into the mixing space through the at least one opening in the junction member. A second fluid, such as a fluid carrying an analyte, is moved by the fluid source into the mixing space through the first conduit. The fluid source may comprise a separator apparatus, such as a liquid chromatography apparatus, a capillary electrophoresis apparatus, or a capillary electrochromatography apparatus. A pressure source, such as pressurized nitrogen, communicates with the interior region of the container to pressurize the interior region of the container so that the first fluid is forced into the mixing space through the at least one opening in the junction member. The first and second fluids are mixed in the mixing space and then the mixture is moved through the second conduit out of the container due to the pressurization of the interior region of the container.

While the disclosed fluid treatment devices may be used to treat fluid that is from any source and that is destined for any subsequent use, certain disclosed devices are especially useful in treating separation effluent from either mechanically or electrically driven separations for subsequent use and analysis. The first fluid or treatment liquid contained in the container may be used to change the pH, density or ionic strength of the second fluid, for example. In some illustrative embodiments, the fluid treatment device is used to create an effluent by adding a buffer material and/or a matrix material to an analyte for subsequent MALDI MS analysis of the effluent.

In one disclosed embodiment, the first conduit is a CE/CEC capillary, the junction member is tubular sleeve defining a channel between the CE/CEC capillary and a deposition conduit. In this embodiment, a buffer material and/or matrix material in the container is electrically conductive and the container includes an electrical pathway, such as a pathway to ground, for completing an electrical circuit. Also in this embodiment, an effluent/buffer matrix mixture is delivered under pressure through the deposition conduit to a MALDI substrate that is used for subsequent MALDI MS analysis, for example.

Additional features of the invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 1 is a diagrammatic view showing a fluid treatment device having a container filled partially with a first fluid, a pressure source for pressurizing the container, a fluid source for delivering via a delivery conduit a second fluid to a junction member situated within the container, and a deposition conduit coupled to the junction member to receive a mixture of the first and second fluids, and also showing a conduit positioner coupled to a lower end of the deposition conduit outside the container to position the lower end of the deposition conduit relative to a substrate that is coupled to a substrate-support apparatus;

FIG. 2 is a perspective view of the junction member and portions of the delivery conduit and the deposition conduit coupled to the junction member showing a mixing space defined between the lower end of the delivery conduit and the upper end of the deposition conduit and showing a pair of openings in the junction member communicating with the mixing space;

DETAILED DESCRIPTION OF THE DRAWINGS

Figure 3:
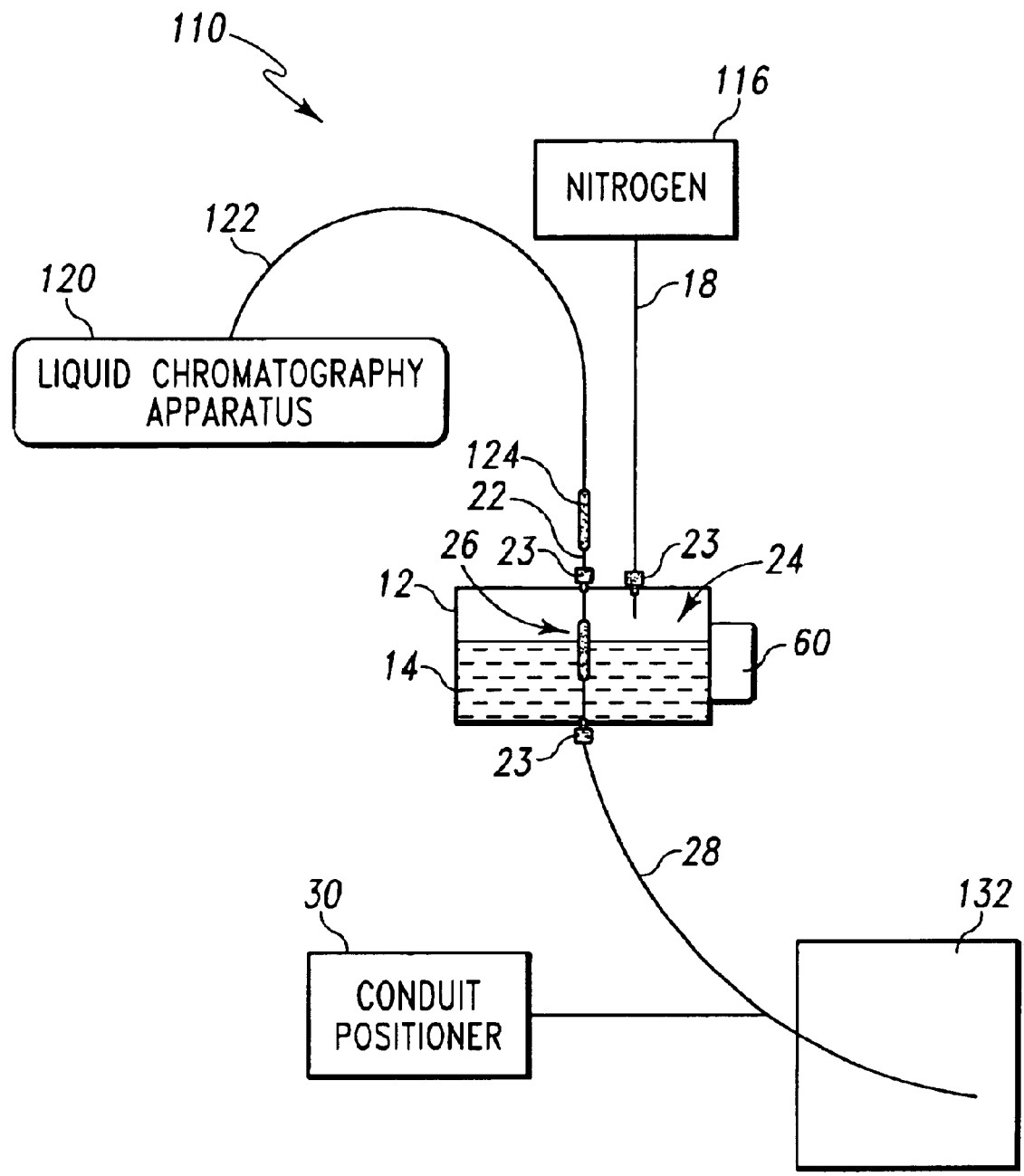
FIG. 3 is a diagrammatic view, similar to FIG. 1, showing an alternative fluid treatment device having a source of nitrogen pressurizing a container filled partially with a matrix material, a liquid chromatography apparatus coupled via a separation conduit to an intermediate sleeve, a delivery conduit extending between the intermediate sleeve and a junction member situated in the container, and a deposition conduit coupled to the junction member to receive a mixture of the matrix material and a fluid carrying an analyte.

A fluid treatment device 10 has a container or vial 12 filled partially with a first fluid 14, a pressure source 16 for pressurizing container 12 through a pressure conduit 18, a fluid source 20, and a delivery conduit 22 through which a second fluid (not shown) flows from fluid source 20 into an interior region 24 of container 12 as shown in FIG. 1. Device 10 further comprises a junction member 26 that is situated in interior region 24 of container 12. Conduit 22 is coupled to junction member 26. Device 10 also has a deposition conduit 28 that is coupled to junction member 26 and that exits container 12. First fluid 14 and the second fluid from source 20 are mixed together within junction member 26 and are moved out of container 12 through conduit 28. A set of nuts 23 provide a fluid-tight connection between respective conduits 18, 22, 28 and container 12. Nuts 23 thread into the various apertures (not shown) that are formed in container 12 for passage of conduits 18, 22, 28 therethrough.

A conduit positioner 30 is coupled to a lower region of conduit 28 and is operable to position conduit 28 relative to a substrate 32 or any other suitable fluid receiver which is configured to receive the mixture of fluids from conduit 28. The terms "substrate" and "fluid receiver" are used herein interchangeably. In some embodiments, substrate 32 is coupled to a substrate positioner 33 that is operable to position substrate 32 relative to conduit 28. In other embodiments, substrate positioner 33 is omitted.

In some embodiments, junction member 26 comprises a connection sleeve, shown in FIG. 2, which is tubular and which is sometimes referred to herein as "sleeve 26." Sleeve 26 has an inner surface 34 that defines an axially extending, main passage between a first end 36 and a second end 38 of sleeve 26. Sleeve 26 also has one or more openings 40 that extend from an outer surface 42 of sleeve 26 to surface 34. In the illustrative embodiment, sleeve 26 has two openings 40 that are bounded by cylindrical surfaces 42 which are formed about midway between ends 36, 38 of sleeve 26 and which extend through sleeve 26 in perpendicular relation with the main passage defined by surface 34. Also in the illustrative embodiment, surfaces 34, 42 are cylindrical.

An exit end 46 of conduit 22 is received in an upper portion of the main passage of member 26 and an entrance end 48 of conduit 28 is received in a lower portion of the main passage of member 26 as shown in FIG. 2. Ends 46, 48 of conduits 22, 28, respectively, are positioned within the main passage of member 26 such that a downwardly facing end surface 50 of conduit 22 is spaced from an upwardly facing end surface 52 of conduit 28 to define a mixing space 54 therebetween. Thus, illustrative sleeve 26 is oriented vertically having the main passage extending vertically and having openings 40 extending horizontally. Mixing space 54 is in fluid communication with interior region 24 of container 12 through openings 40. Sleeve 26 holds end 46 of conduit 22 and end 48 of conduit 28 in alignment. Sleeve 26 may be omitted in embodiments having rigid conduits 22, 28 that are held in alignment by nuts 23 or by other mechanisms suitable for maintaining the alignment of conduits 22, 28. It is within the scope of this disclosure for end 46 of conduit 22 to abut end 48 of conduit 28 and for either or both of end surfaces 50, 52 to have notches, grooves, channels, or the like to provide fluid communication between interior region 24 of container 12 and passages 56, 62 of conduits 22, 28 respectively.

Container 12 is filled with enough fluid 14 to ensure that an upper surface 58 of fluid 14 is above openings 40 in junction member 26. However, container 12 is not completely filled with fluid 14 so that the portion of interior region 24 of container above surface 58 is pressurizable by pressure source 16. Thus, the lower end of conduit 18 terminates in space 24 above surface 58 of fluid 14 as shown in FIG. 1. Illustratively, a cap 60 is coupled to container 12 to block an inlet port (not shown) through which fluid 14 is introduced into container 12 when cap 60 is removed. Pressurization of interior region 24 of container 12 by pressure source 16 forces a quantity of fluid 14 to move through opening 40 into mixing space 54. In addition, fluid source 20 is operable to move the second fluid through an internal passage 56 of conduit 22 and into mixing space 54 where the second fluid mixes with fluid 14. The pressure created in interior region 24 of container 12 causes the mixture of the first fluid 14 and the second fluid to move downwardly through an internal passage 62 of conduit 28. The mixture of the first fluid 14 and the second fluid exits the lower end of conduit 28 as an effluent for further handling and/or processing and/or analysis as desired.

It is contemplated by this disclosure, that the first fluid 14 and the fluid from fluid source 20 may be any desired fluids that are to be mixed together for any subsequent use. However, fluid treatment devices in accordance with the teachings of this disclosure are especially useful in treating separation effluent from either mechanically or electrically driven separations for subsequent use and analysis. In some fluid treatment devices, fluid source 20 comprises a separation apparatus that operates to separate an analyte into its constituent molecules. In some of these fluid treatment devices, the first fluid 14 in container 12 serves as a treatment liquid that may be used to change the pH, density, or ionic strength of the second fluid, for example. As also contemplated herein, the treatment liquid in container 12 may comprise a buffer material and/or a matrix material that is added to an analyte to create an effluent for subsequent MALDI MS analysis of the effluent.

Referring now to FIG. 3, an alternative fluid treatment device 110 that uses liquid chromatography is provided. Device 110 is similar to device 10 in many respects and therefore, like reference numerals used to denote elements of device 110 that are substantially similar to like elements of device 10. One difference between device 10 and device 110 is that the generic pressure source 16 of device 10 is replaced in device 110 with a source 116 of pressurized nitrogen. It is understood that any non-reactive, ideal gas may be used in lieu of nitrogen to pressurize container 12. Another difference between device 10 and device 110 is that the generic fluid source 20 of device 10 is replaced in device 110 with a liquid chromatography apparatus 120, a separation conduit 122, and an intermediate sleeve 124. Furthermore, a stationary phase material is packed in conduit 122 of device 110. Apparatus 120 includes equipment, such as an Agilent 110 series liquid chromatography pump for moving an analyte into conduit 122 and a splitter for controlling the flow of the analyte into conduit 122.

In some fluid treatment device embodiments using liquid chromatography, packed capillary columns are coupled directly to sleeve 26 in the same manner as described above regarding connection of conduit 22 to sleeve 26. In embodiments having a micro column, intermediate sleeve 124 is used prior to interfacing with sleeve 26 as shown in FIG. 3. Illustratively, sleeve 124 connects conduit 122 to conduit 22. In some fluid treatment devices using liquid chromatography, fluid 14 is a matrix material that is mixed in space 54 of sleeve 26 with the effluent carrying an analyte from apparatus 120. In such embodiments, the resultant, mixed effluent may be deposited on a MALDI plate 132 and then analyzed by MALDI/TOF/MS. Illustrative plate 132 is made from stainless steel, for example.

Figure 4:
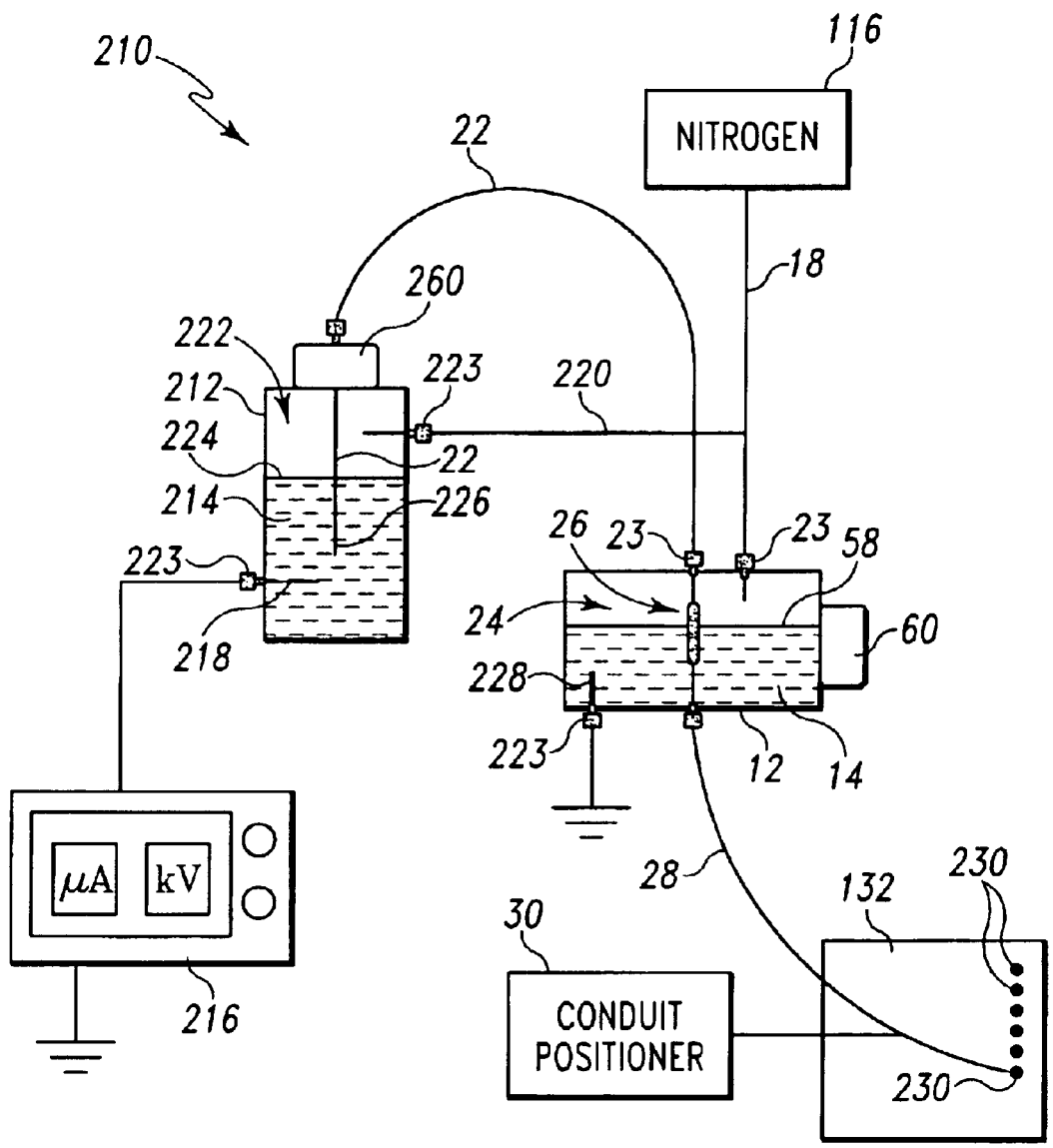
FIG. 4 is a diagrammatic view, similar to FIG. 3, showing another alternative fluid treatment device having a source of nitrogen pressurizing a container filled partially with a matrix material, a capillary electrochromatography (CEC) apparatus coupled via a delivery conduit to a junction member situated in the container, and a deposition conduit coupled to the junction member to receive a mixture of the matrix material and a fluid carrying an analyte.

Referring now to FIG. 4, an alternative fluid treatment device 210 that uses capillary electrochromatography (CEC) is provided. Device 210 is similar to devices 10, 110 in many respects and therefore, like reference numerals used to denote elements of device 210 that are substantially similar to like elements of devices 10, 110. In lieu of generic fluid source 20 of device 10 and elements 120, 122, 124 of device 110, device 210 has a container 212 that contains a fluid 214 which flows from container 212 through conduit 22 to junction member 26 in container 12. Device 210 also has a power supply 216, such as a high voltage power supply of the type available from Spellman High Voltage Electronics of Plainview, N.J. Power supply 216 outputs an electrical potential that is adjustable, in some embodiments, between 0 Volts and 40 kilovolts and that is applied to fluid 214 via an electrode 218 which is immersed in fluid 214. In some embodiments, electrode 218 is made of platinum. Fluid 214 is electrically conductive and becomes electrically charged by the electrical potential applied thereto.

Another difference between device 210 and devices 10, 110 is that device 210 has an auxiliary pressure conduit 220 through which pressurized nitrogen gas is communicated from conduit 18, or alternatively from source 116, to an interior region 222 of container 212. Specifically, pressurized nitrogen gas is introduced into container 212 above an upper surface 224 of fluid 214. It is understood that any non-reactive, ideal gas may be used in lieu of nitrogen to pressurize container 212. An entrance end 226 of conduit 22 is submerged in fluid 214 and pressurization of container 212 is substantially equalized with pressurization of container 12. The electrical potential created by power supply 216 causes a quantity of electrically charged fluid 214 to moves through end 226, into passage 56 of conduit 22, and then on to junction member 26. Illustrative junction member 26 of device 210 is made from a material that is an electrical insulator, such as a Silica Seal Tight™ sleeve available from Upchurch Scientific of Oak Harbor, Wash. In alternative embodiments, junction member 26 is made from other materials suitable for holding ends 46, 48 of conduits 22, 28, including electrically conductive materials.

Device 210 has an electrode 228 that is immersed in fluid 14 and that is coupled electrically to ground. In some embodiments, electrode 228 is made of platinum. Fluid 14 used in device 10 is a buffer material and/or matrix material that is electrically conductive. Thus, an electrical pathway forming a complete electrical circuit is provided via power supply 216, electrode 218, fluid 214 in container 212 and in conduit 22, a mixture of fluid 214 and fluid 14 in mixing space 54 of sleeve 26, fluid 14 in container 12, and electrode 228. Power supply 216 and electrode 228 are both coupled electrically to ground. The mixture of fluid 14 and fluid 214, which includes an analyte, produces a resultant effluent 230 that is moved through conduit 28 and deposited on an ungrounded MALDI plate 132 for subsequent analysis by MALDI/TOF/MS. Conduit 28 and plate 132 are excluded from the electrical pathway of device 210 and therefore, need not be grounded.

An additional set of nuts 223 are included in device 210 to provide fluid-tight connections between electrodes 218, 228 and respective containers 212, 12, between conduit 220 and container 212, and between conduit 22 and a cap 260 that is coupled to container 212 as shown in FIG. 4. Nuts 223 thread into the various apertures (not shown) that are formed in containers 12, 212 and in cap 260 for passage of respective electrodes 218, 228 and conduits 22, 220 therethrough. Cap 260 blocks an inlet port (not shown) through which fluid 214 is introduced into container 212 when cap 260 is removed. In alternative embodiments of device 210, capillary electrophoresis (CE) techniques are used for separation of an analyte into its constituent molecules in lieu of the disclosed capillary electrochromatography techniques.

In some embodiments in which an analyte is separated into its constituent molecules, such as the embodiment shown in FIG. 4, conduit 22 has an outside diameter (o.d.) of 365 micrometers ($\mu$m), has an inside diameter (i.d.) (i.e., the diameter of passage 56) of 100 $\mu$m, and is made from fused silica that is coated with polyamide to provide a high degree of flexibility. In the embodiments of FIG. 4, conduit 28 has an o.d. of 365 $\mu$m, has an i.d. (i.e., the diameter of passage 62) of 25 $\mu$m, and is also made from fused silica coated with polyamide. Further details regarding procedures for preparing conduits 22, 28 may be found in the following publications which are hereby incorporated by reference herein: Palm, A. and Novotny, M. V. *Anal. Chem.* 1997, 69, 4499–4507; Que A. H., Palm, A., Baker, A. G., and Novotny, M. V. *J. Chromatogr. A* 2000, 877, 379–391. Fused silica is available from Polymicro Technologies of Phoenix, Ariz. In alternative embodiments, including devices 10, 110, conduits 22, 28 may be made from other materials, such as stainless steel or polyethylketone (PEEK).

Also in the embodiment of FIG. 4, junction member 26 has an o.d. of 1/16 inch (1587.5 $\mu$m) and has an i.d. of 330 $\mu$m. Thus, conduits 22, 28 having an o.d. of 365 $\mu$m are press fit into connection sleeve 26 having an i.d. of 330 $\mu$m. In addition, the i.d. of conduit 22 is approximately four times the size of the i.d. of conduit 28 in the illustrative embodiment of FIG. 4. In the embodiment of FIG. 4, openings 40 are formed through junction member 26 by using a drill bit having an o.d. of 400 $\mu$m. Thus, the i.d. of openings 40 are approximately 400 $\mu$m. Prior to insertion of ends 46, 48 of conduits 22, 28, respectively, into the main passage of connection sleeve 26, a capillary or strand (not shown) having an o.d. of 160 $\mu$m is inserted through openings 40. Thereafter, ends 46, 48 of conduits 22, 28, respectively, are inserted into the main passage of connection sleeve 26 until end surfaces 50, 52 of conduits 22, 28, respectively, contact the 160 $\mu$m o.d. capillary. Once ends 46, 48 of conduits 22, 28, respectively, are positioned in the main passage of connection sleeve 26, the 160 $\mu$m o.d. capillary is removed from passages 40. Thus, the 160 $\mu$m o.d. capillary acts as a gauge to ensure that end surfaces 50, 52 of conduits 22, 28, respectively, are spaced apart by approximately 160 $\mu$m.

In some embodiments, container 12 is made from Delrin® material and has the following dimensions: 2.25 inches in height, 1.5 inches in width, and 1.25 inches in depth. In such embodiments, a 0.5 inch hole may be drilled into the center of container 12 to contain fluid 14, such as a buffer and/or matrix material. Container 212 may also be made from Delrin® material and have dimensions similar to container 12. In addition, Teflon® o-rings may be used to seal and sustain the pressures applied to containers 12, 212. These o-rings may be present between cap 60 and container 12 and between cap 260 and container 212. In addition, nuts 23, 223 have sleeves that seal against the respective conduits 18, 22, 28, 220 and electrodes 218, 228 when nuts 23, 223 are tightened in a manner well-known to those skilled in the art.

The pressure applied to container 12 by source 16 or source 116, as the case may be, affects the rate at which effluent flows from deposition conduit 28. In some embodiments, the pressure applied to the interior region 24 of container 12 is variable between 5 and 30 pounds per square inch (p.s.i.). In addition, the rate at which fluid enters mixing space 54 through conduit 22 is controllable by, for example, varying the manner in which source 20 is operated, such as by varying a pressure differential between source 20 and container 12 (in the case of device 10); varying the pump speed of apparatus 120, varying the amount that one or more valves of apparatus 120 is opened or closed, or varying the operation of the splitter of apparatus 120 (in the case of device 110); or varying the electrical potential applied to electrode 218 by power supply 216 (in the case of device 210).

In embodiments having conduits 22, 28 and sleeve 26 dimensioned as described above, the fluid 14 flows through openings 40 into mixing space 54 at a rate of approximately 160 nanoliters per minute, the fluid from the liquid chromatography apparatus of FIG. 3 flows through conduit 22 into mixing space 54 at a rate of approximately 150 nanoliters per minute, and the fluid from the capillary electrochromatography apparatus of FIG. 4 flows through conduit 22 into mixing space 54 at a rate of approximately 40 nanoliters per minute. It should be appreciated that the diameter or size of openings 40, the number of openings 40, the diameter or size of passage 56, the diameter or size of passage 62, the size of mixing space 54, the spacing between end surfaces 50, 52, the viscosity of the first fluid, and the viscosity of the second fluid all have an effect on the rate at which the effluent mixture of the first and second fluids flow from conduit 28. The above-listed parameters also have an effect on the proportions of the first and second fluids in the effluent mixture emerging from conduit 28. By routine experimentation, desired flow rates of effluent emerging from conduit 28 and desired proportions of the first and second fluids in the effluent emerging from conduit 28 may be obtained.

In one embodiment of device 210, a stationary phase material packed into conduit 22 consisted of 5% T, 60% C {Hjerten's designation (Hjerten, S. *Arch. Biochem. Biophys.*

1962, Supl 1, 147–151) defines T and C and is hereby incorporated by reference herein}, 3% polyethylene glycol (PEG, MW 10,000), 40% 2-cyanoethylacrylate (CEA) and 10% vinylsulfonic acid. In this embodiment, a monomer solution or reaction mixture may be prepared by dissolving 10.0 milligrams (mg) acrylamide, 30 mg N,N'-methylene-bis-acrylamide, 16.0 microliters ($\mu$L) CEA, 12.4 $\mu$L vinylsulfonic acid and 30 mg PEG in 0.5 milliliters (mL) formamide and 0.5 mL 100 millimoles (mM) Tris—150 mM boric acid (pH 8.2). Also in this embodiment, polymerization may be initiated using 4 $\mu$L of 20% (v/v) N,N,N',N'-tetramethylenediamine (TEMED) and 4 $\mu$L of 40% ammonium persulfate added to 0.5 mL of the above monomer solution heated to 50 degrees Celsius. This polymerization proceeds for a fairly lengthy period of time, such as overnight, at room temperature. Subsequently, conduit 22 with such stationary phase material is flushed and conditioned using a solution consisting of 50:50 (v/v) acetonitrile: 5 mM phosphate buffer at pH 3.0. Acrylamide and N,N'-methylene-bis-acrylamide are available from BioRad Laboratories of Hercules, Calif. Ammonium persulfate, TEMED, 3-methacryloxypropyltrimethoxysilane (Bind-Silane), and PEG are available from Sigma Company or St. Louis, Mo. Vinylsulfonic acid (sodium salt, 25% (v/v)), CEA, and formamide are available from Aldrich of Milwaukee, Wis.

Figure 5:
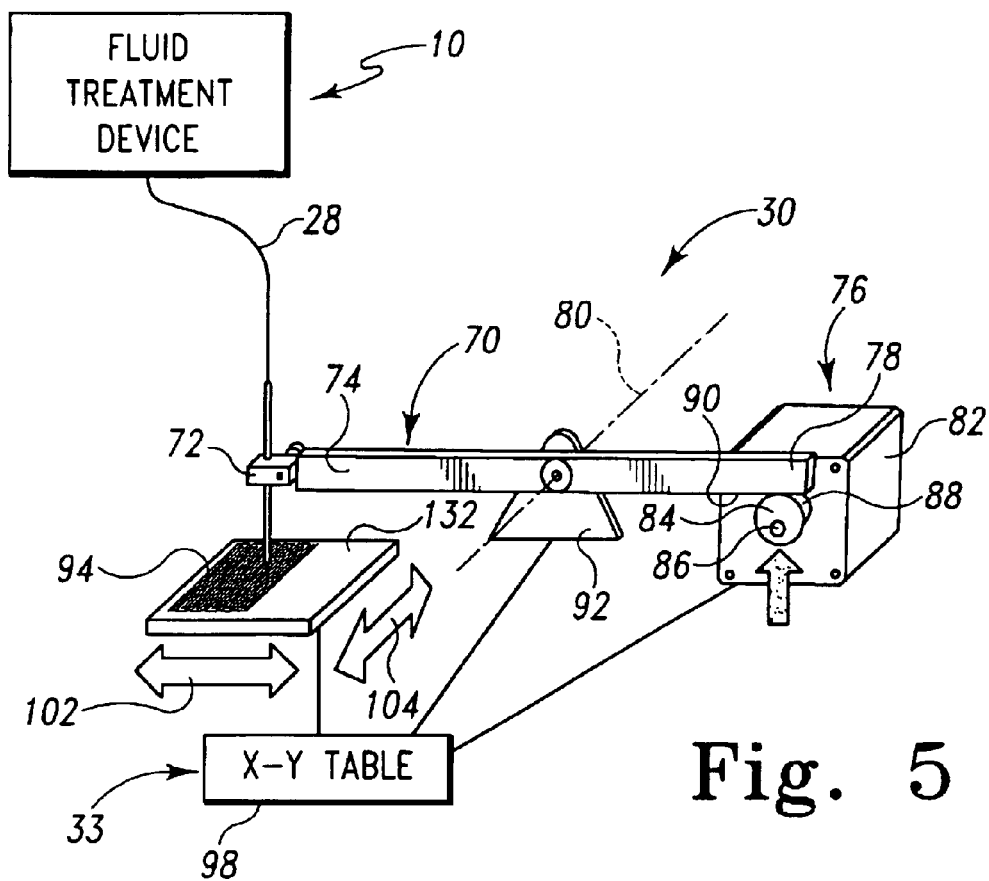
FIG. 5 is a diagrammatic view showing a conduit positioner having a pivotable arm that is driven by a cam mounted to an output shaft of a motor of the conduit positioner, the conduit positioner having a coupler for coupling a first end of the arm to a lower end of a deposition conduit that extends from a fluid treatment device, and a MALDI plate situated beneath the lower end of the deposition conduit and being moved in orthogonal horizontal directions so that effluent exiting the lower end of the deposition conduit is deposited on the MALDI plate in a substantially continuous, serpentine pattern.
Figure 6:
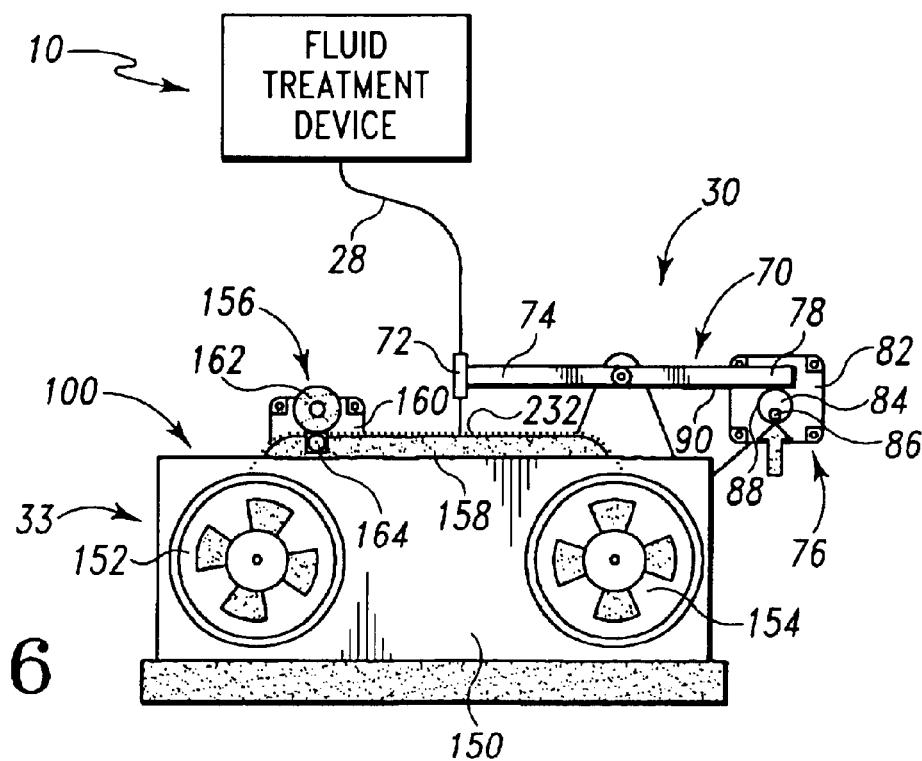
FIG. 6 is a diagrammatic view showing the conduit positioner of FIG. 5 being operated to deposit spots of effluent on a tape that is advanced by a reel-to-reel machine from a first reel to a second reel.

As mentioned above, conduit positioner 30 is coupled to a lower region of conduit 28 and is operable to position conduit 28 relative to any suitable fluid receiver, such as substrate 32 or MALDI plate 132, and the fluid receiver is coupled to a substrate positioner 33 that is operable to position the fluid receiver relative to conduit 28. FIGS. 5 and 6 show fluid treatment device 10 being used with positioners 30, 33. However, any fluid treatment device, including devices 10, 110, 210 disclosed herein, may be used with positioners 30, 33 to deposit effluent, such as effluent emerging from conduit 28, on a fluid receiver. Illustratively, conduit positioner 30 comprises an arm 70, a coupler 72 that couples the lower region of conduit 28 to a first end 74 of arm 72, and a driver 76 that acts upon a second end 78 of arm 70 to pivot arm 70 about a pivot axis 80 as shown in FIG. 5. In some embodiments, the orientation of coupler 72 relative to arm 70 is adjustable to change the orientation of the lower end of conduit 28 relative to arm 70.

Operation of driver 76 pivots arm 70 about axis 80 to move the lower end of conduit 28 between a raised position and a lowered position. Illustrative driver 76 comprises a motor 82 and a cam 84 that is mounted to an output shaft 86 of motor 82. Operation of motor 82 rotates output shaft 86 along with cam 84 so that a cam surface 88 of cam 84 wipes against a bottom surface 90 of arm 70, thereby pivoting arm about axis 80. Substrate positioner 30 has a biaser (not shown), such as a torsion spring or tension spring, that acts between arm 70 and some other stationary structure, such as illustrative flange 92 to which arm 70 is pivotably coupled, to bias end 78 of arm 70 into engagement with cam 84. In some alternative embodiments, driver 76 comprises a linear stepper motor, and in other alternative embodiments, driver 76 comprises a solenoid.

In one mode of operation of positioners 30, 33, arm 70 is pivoted by driver 76 to a first orientation having the lower end of conduit 28 in the lowered position, either touching or in close proximity to the fluid receiver, such as illustrative MALDI plate 132, and then arm 70 is held stationary by driver 76. When arm 70 is held stationary in the first orientation, substrate positioner 33 may then be operated to maneuver the fluid receiver beneath the lower end of conduit 28 so that a substantially continuous line, film, or trace of effluent is deposited on the fluid receiver in a desired pattern. In an illustrative example of the first mode of operation of positioners 30, 33, shown in FIGS. 5 and 7, continuous trace 94 is deposited on MALDI plate 132 in a serpentine pattern.

Figure 8:
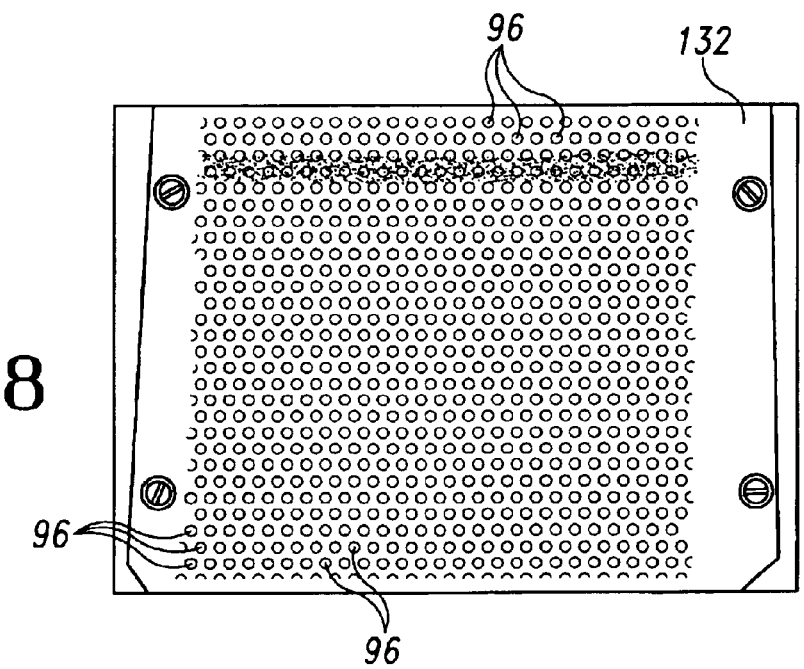
FIG. 8 is a top plan view of a MALDI plate showing a pattern of spots of effluent deposited on the MALDI plate by the conduit positioner of FIG. 5 when the motor is operated to cyclically pivot the arm to raise and lower the lower end of the deposition conduit relative to the MALDI plate.

In a second mode of operation of positioners 30, 33, arm 70 is cyclically reciprocated between the first orientation and a second orientation so that the lower end of conduit 28 is cycled repeatedly between the lowered position, either touching or in close proximity to the fluid receiver, and the raised position, spaced from the fluid receiver by a sufficient distance to prevent effluent from being deposited on the fluid receiver. Such reciprocation of arm 70 occurs, for example, when shaft 86 and cam 84 are continuously rotated. As the lower end of conduit 28 is cycled between the raised and lowered positions, substrate positioner 33 may be operated to index the fluid receiver in a desired manner so that spots or aliquots 96 of effluent are deposited on the fluid receiver in a desired two-dimensional array. An example of such a two dimensional array of aliquots 96 deposited on MALDI plate 132 is shown in FIG. 8.

According to this disclosure, positioners 30, 33 and conduit 28 cooperate to provide a device for placement of effluent on a substrate or any other suitable fluid receiver. The effluent may be delivered to conduit 28 by any means, including the fluid treatment devices disclosed herein. In one illustrative embodiment, positioner 33 comprises an X-Y table 98, as shown diagrammatically in FIG. 5, and in another embodiment, positioner 33 comprises a reel-to-reel tape drive 100, as shown in FIG. 6. X-Y table 98 supports the fluid receiver, such as plate 132, for bidirectional horizontal movement in an x-direction, indicated by double-headed arrow 102 in FIG. 5, and in a y-direction, indicated by double-headed arrow 104 in FIG. 5. Y-direction 104 is orthogonal to x-direction 102. Flange 92 and drive 76 may be coupled to X-Y table 98 as shown diagrammatically in FIG. 5. Alternatively, flange 92 and drive 76 may be coupled to some other structure adjacent table 98.

Reel-to-reel tape drive 100 comprises a housing 150, a source reel 152 supported for rotation relative to housing 150, a destination reel 154 supported for rotation relative to housing 150, and a motor-driven capstan pinch roller assembly 156 that operates to move a polymer tape 232 from reel 152 to reel 154 across a tape-support member 158. In this embodiment, tape 232 serves as the fluid receiver. Assembly 156 includes a motor 160, an upper roller 162, and a lower roller 164. Tape 232 is routed between rollers 162, 164 in contact therewith. At least one of rollers 162, 164 is driven by motor 160 to feed tape 232 across member 158. In alternative embodiments, drive 100 has at least one motor in housing 150 that drives one or both reels 152, 154 to move tape 232 from reel 152 to reel 154 across member 158. Flange 92 and drive 76 may be coupled to housing 150 of drive 100 or to some other structure adjacent drive 100.

In the first mode of operation, in which arm 70 is held stationary in the first orientation, effluent exiting conduit 28 is deposited on tape 232 as a substantially continuous straight-line trace as tape 232 is driven from reel 152 to reel 154. In the second mode of operation, in which arm 70 is reciprocated cyclically between the first and second orientations, effluent exiting conduit 28 is deposited on tape 232 as a series of spots or aliquots 96 as tape 232 is driven from reel 152 to reel 154. An example of spots 96 on a segment of tape 232 produced by the second mode of operation is shown in FIG. 9.

Figure 7:
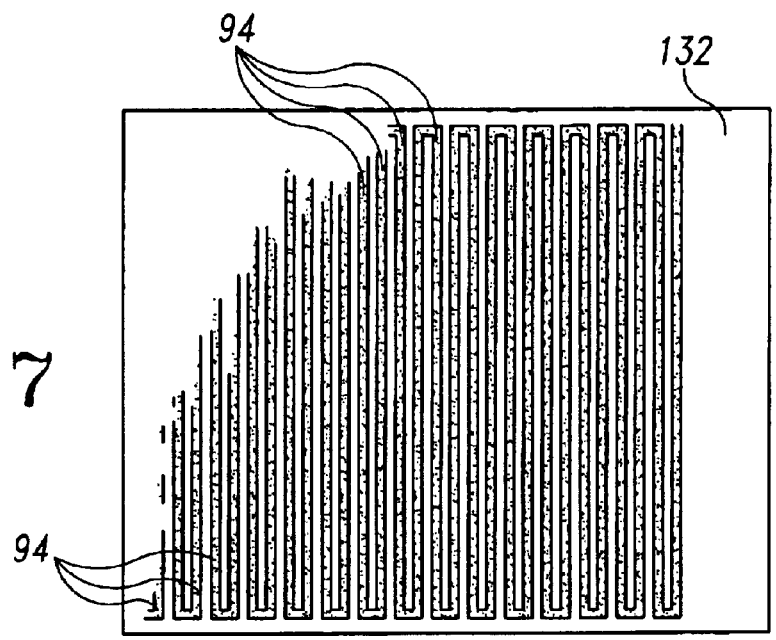
FIG. 7 is top plan view of the MALDI plate of FIG. 5 after effluent is deposited thereon in the serpentine pattern.
Figure 9:
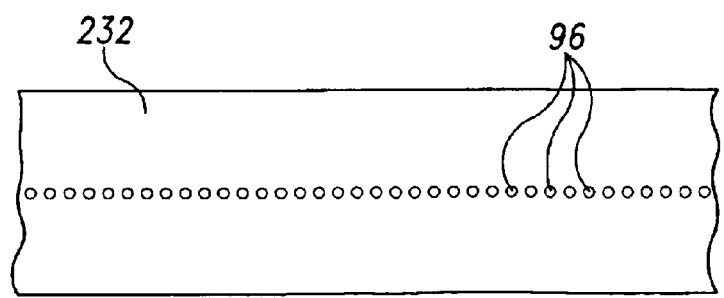
FIG. 9 is a top plan view of a portion of the tape of FIG. 6 showing a pattern of spots of effluent deposited on the tape by the conduit positioner when the motor is operated to cyclically pivot the arm to raise and lower the lower end of the deposition conduit relative to the tape.

In the illustrative examples of FIGS. 7–9, the effluent of trace 94 and spots 96 comprises an α-cyano-4- hydroxycinnamic acid solution in aceotnitrile/water at a concentration of 10 milligrams per milliliter (mg/ml). The diameters of spots 96 in the examples of FIGS. 8 and 9 are approximately 70 μm. However, varying the speed that drive 76 moves arm 70 between the first and second orientations and varying the speed of the fluid receiver, such as plate 132 or tape 232, affects the spot position, spacing, and size. In some embodiments, conduit positioner 30 and substrate positioner 33 have separate controllers (i.e. computers, microcontrollers, programmable logic controllers, microprocessors, and the like) and associated user inputs to permit users to control positioners 30, 33 separately. Software may be stored in memory devices of such controllers and executed by the controllers to command the operation of positioners 30, 33. In other embodiments, a single controller and associated user inputs are coupled to both positioners 30, 33 to coordinate the operation of positioners 30, 33 simultaneously.

Fluid treatment devices 10, 110, 210 operate such that effluent emerges continuously from the lower end of conduit 28 due to the continuous pressurization of container 12 by source 16 or source 116, as the case may be. Thus, when the lower end of conduit 28 is held by arm 70 away from the fluid receiver, surface tension of the effluent adjacent the opening in the lower end of conduit 28 prevents the effluent from separating from the lower end of conduit 28. When the lower end of conduit 28 moves into the lowered position, the effluent adjacent the opening in the lower end of conduit 28 contacts and adheres to the fluid receiver, such as substrate 32, plate 132, or tape 232.

The positioners 30, 33 disclosed herein allow for the controlled, high-volume, high-speed, automated placement of effluents on fluid receivers, such as substrates, plates, and tapes. When used with fluid treatment devices, such as devices 110, 210, having separator apparatus that separates analytes into constituent molecules, positioners 30, 33 are able to produce quickly, a large number of samples to be analyzed using MALDI/TOF/MS. In addition, due to pressurization of container 12, which results in effluent moving from mixing space 54 through conduit 28, deposition of the effluent emerging from conduit 28 on fluid receivers may take place in the ambient atmosphere. This is in contrast to some prior art systems in which effluent is deposited on MALDI plates in a vacuum.

Illustrative substrate positioner 33, therefore, serves as a moveable, controllable workpiece holder and illustrative conduit positioner 30 serves as a moveable, controllable holder for a sample-dispensing conduit 28 for preparing samples for MALDI MS analysis. Information stored in memory devices of the controllers associated with positioners 30, 33 may be combined with or correlated to information about the source and/or test results of various traces, portions, or aliquots of the sample material that is stored in a database resident on another computer device.

Figure 10:
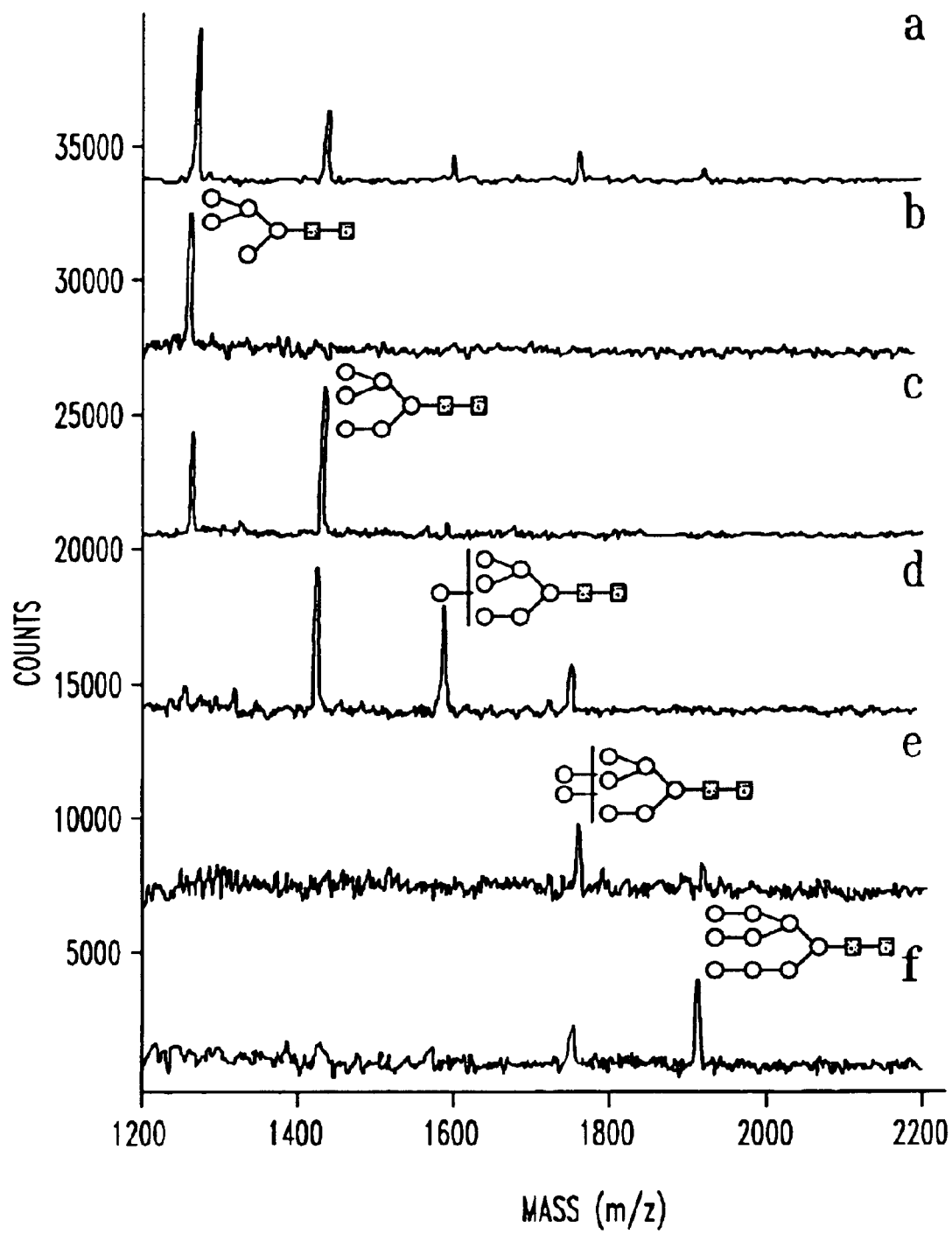
FIG. 10 is graph of a CEC-MALDI analysis of N-glycans derived from Ribonuclease B showing an "a" trace depicting a mass spectrum of a mixture of the N-glycans and showing "b–f" traces depicting the spectra of different aliquots deposited on a MALDI plate after CEC separation.
Figure 11:
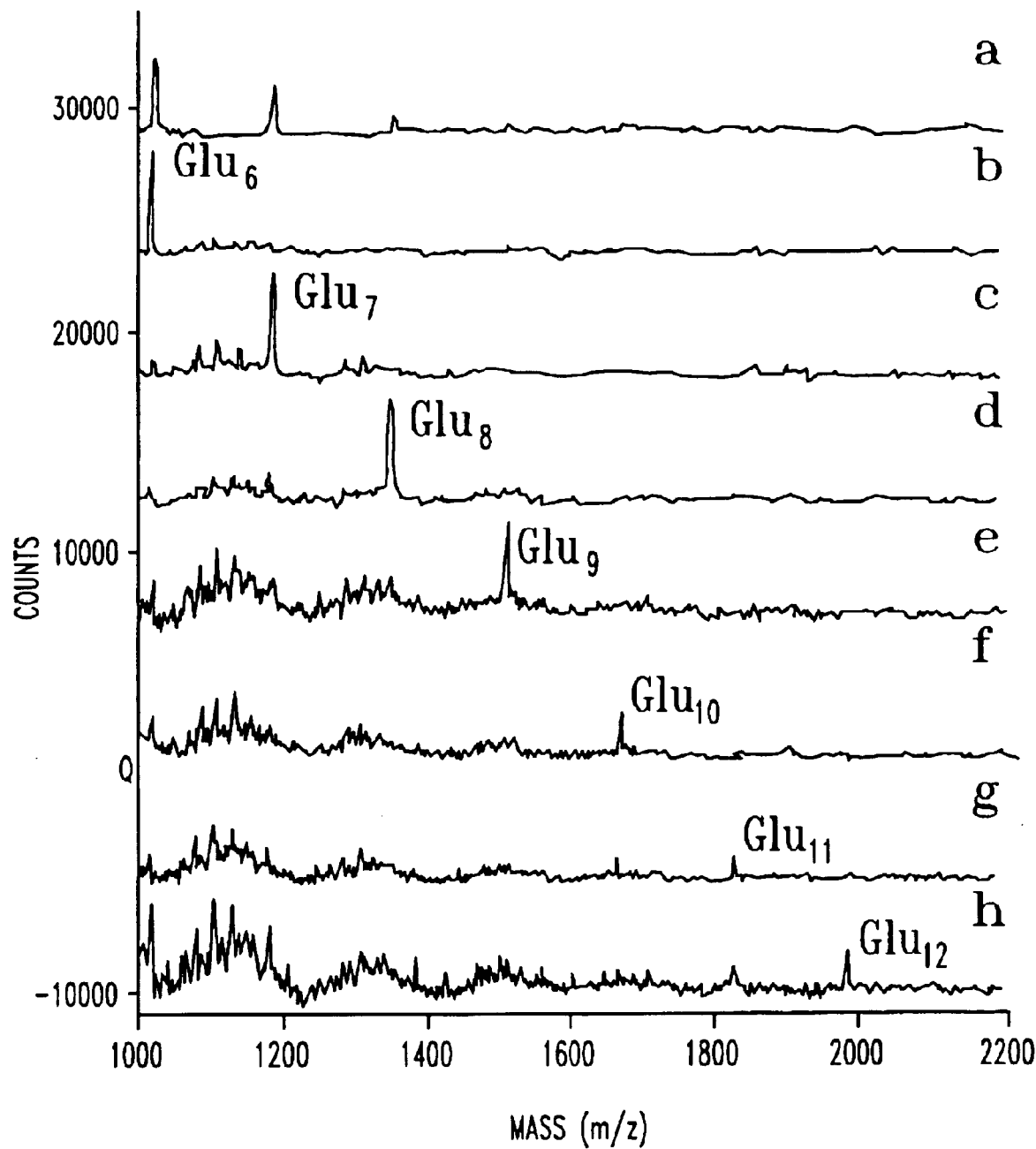
FIG. 11 is a graph of a CEC-MALDI analysis of Dextrin showing an "a" trace depicting a mass spectrum of the Dextrin mixed with a matrix material and showing "b–f" traces depicting the spectra of different aliquots deposited on a MALDI plate after CEC separation.

As mentioned previously, the fluid treatment devices and the effluent placement devices disclosed herein are used to deposit effluent on a substrate for subsequent analysis by matrix-assisted laser desorption ionization time-of-flight mass spectrometry (MALDI/TOF/MS). Effluents deposited on substrates in the manner described herein may also be analyzed with MS analyzers employing other techniques, such as, for example, quadrapole time-of-flight (QTOF) techniques, Fourier transform ion cyclotron resonance (FTICR) techniques, and ion trap (IT) techniques. In some such embodiments, the effluent placed on the substrate comprises a mixture of an analyte and a matrix material. Examples of graphs produced by MALDI/TOF/MS are shown in FIGS. 10 and 11. The mass spectra examples in FIGS. 10 and 11 were produced with a Voyager-DE™ RP Biospectrometry™ Workstation instrument which was equipped with a pulsed nitrogen laser (337 nanometers) and which is available from Applied Biosystems of Framingham, Mass. The MALDI mass spectra were acquired at 25 kV and 18 kV accelerating voltage in the positive-ion mode, while the low-mass gate was used to discard ions with m/z values of less than 400. All acquired spectra were smoothed by applying a 19-point Savitzky-Golay smoothing routine, such as is described in Savitzky, A.; Golay, M. J. E. *Anal. Chem.*, 1964, 36, 1627–1638 which is hereby incorporated by reference herein. The instrument was calibrated with a standard dextrin ladder.

The example shown in FIG. 10 is graph of a CEC-MALDI analysis of N-glycans derived from Ribonuclease B showing an "a" trace depicting a mass spectrum of a mixture of the N-glycans and showing "b–f" traces depicting the spectra of different aliquots deposited on a MALDI plate after CEC separation. The example shown in FIG. 11 is a graph of a CEC-MALDI analysis of Dextrin showing an "a" trace depicting a mass spectrum of the Dextrin mixed with a matrix material and showing "b–f" traces depicting the spectra of different aliquots deposited on a MALDI plate after CEC separation. Ribonuclease B is available from Sigma Company of St. Louis, Mo. Dextrin DE 10 is available from Fluka of Buchs, Switzerland.

Although the invention has been described in detail with reference to certain illustrative embodiments, variations and modifications exist with the scope and spirit of this disclosure as described and defined in the following claims.

What is claimed is:

1. A fluid treatment device for mixing a first fluid and a second fluid, the device comprising
   a container having an interior region in which a quantity of the first fluid is situated,
   a pressure source operable to pressurize the interior region of the container,
   a fluid source from which the second fluid flows,
   a first conduit arranged to deliver the second fluid from the fluid source into the interior region of the container, and
   a second conduit arranged to deliver a mixture of the first and second fluids from the interior region of the container to a location outside the container, an end of the first conduit being aligned with an end of the second conduit, the first and second conduits having substantially equivalent outside diameters, the fluid source being operable to move the second fluid through the second conduit, the first fluid being moved between the ends of the first and second conduits to mix with the second fluid as a result of the interior region of the container being pressurized by the pressure source, and the mixture of the first and second fluids being moved out of the interior region through the second conduit as a result of the interior region of the container being pressurized by the pressure source.

2. The device of claim 1, wherein the fluid source comprises a liquid chromatography apparatus.

3. The device of claim 1, wherein the fluid source comprises a capillary electrochromatography apparatus.

4. The device of claim 1, wherein the fluid source comprises a capillary electrophoresis apparatus.

5. The device of claim 1, further comprising a stationary phase material in the first conduit and the stationary phase material being configured to promote separation of the second fluid into its constituent molecules as the second fluid flows through the first conduit.

6. The device of claim 1, wherein at least one of the first conduit and the second conduit is made from a fused silica material coated with a polyamide material.

7. The device of claim 1, wherein portions of the first and second conduits that are situated in the container are oriented vertically.

8. The device of claim 1, wherein the end of the first conduit is situated above the end of the second conduit.

9. The device of claim 8, wherein the end of the first conduit is spaced from the end of the second conduit to define a mixing space therebetween.

10. The device of claim 1, further comprising a junction member holding the ends of the first and second conduits in alignment.

11. The device of claim 1, wherein the first conduit has a first internal passage of a first inside diameter extending therethrough, the second conduit has a second internal passage of a second inside diameter extending therethrough, and the first diameter is approximately four times the second diameter.

12. The device of claim 11, wherein the first conduit has a first outside diameter, the second conduit has a second outside diameter, and the first outside diameter is substantially equivalent to the second outside diameter.

13. The device of claim 1, wherein the ends of the first and second conduits are located beneath an upper surface of the first fluid contained in the container.

14. A fluid treatment device comprising
a container having an interior region that is pressurizable,
a first conduit having an entrance end outside the interior region and having an exit end in the interior region,
a second conduit having an entrance end inside the interior region and having an exit end outside the interior region, and
a connection sleeve situated in the interior region of the container and having a main passage, the exit end of the first conduit being situated in the main passage, the entrance end of the second conduit being situated in the main passage, a mixing space being defined in the main passage between the exit end of the first conduit and the entrance end of the second conduit, the connection sleeve having at least one opening configured to permit fluid communication between the interior region of the container and the mixing space.

15. The device of claim 14, wherein the exit end of the first conduit is situated above the mixing space and the entrance end of the second conduit is situated beneath the mixing space.

16. The device of claim 14, wherein the main passage is oriented vertically and the at least one opening is oriented horizontally.

17. The device of claim 14, wherein the connection sleeve is made of a material that is electrically insulative.

18. The device of claim 14, wherein the connection sleeve is made of a material that is electrically conductive.

19. The device of claim 14, wherein the connection sleeve comprises a cylindrical tubular member, the main passage extends axially relative to the cylindrical tubular member, and the at least one opening extends radially relative to the cylindrical tubular member.

20. The device of claim 14, wherein at least one of the first conduit and the second conduit is made from a fused silica material coated with a polyamide material.

21. The device of claim 14, wherein portions of the first and second conduits that are situated in the container are oriented vertically.

22. The device of claim 14, wherein the first conduit has a first internal passage of a first inside diameter extending therethrough, the second conduit has a second internal passage of a second inside diameter extending therethrough, and the first diameter is approximately four times the second diameter.

23. The device of claim 22, wherein the first conduit has a first outside diameter, the second conduit has a second outside diameter, and the first outside diameter is substantially equivalent to the second outside diameter.

24. A fluid treatment device for mixing a matrix material and an analyte, the device comprising
a separator apparatus configured to separate the analyte into its constituent molecules,
a container having an interior region in which a quantity of the matrix material is situated,
a pressure source operable to pressurize the interior region of the container,
a junction member situated in the interior region of the container and having a main passage,
a delivery conduit arranged to deliver the analyte through the interior region of the container and into the main passage of the junction member, the delivery conduit having an exit end situated in the main passage, and
a deposition conduit arranged to deliver a mixture of the matrix material and the analyte from the main passage of the junction member and through the interior region of the container to a location outside the container for deposition on a substrate, the deposition conduit having an entrance end situated in the main passage, a mixing space being defined in the main passage between the exit end of the delivery conduit and the entrance end of the deposition conduit, the junction member having at least one opening providing fluid communication between the interior region of the container and the mixing space, the separator apparatus being operable to move the analyte into the mixing space through the exit end of the delivery conduit, the matrix material being moved into the mixing space as a result of the interior region of the container being pressurized by the pressure source, and the mixture of the analyte and the matrix material being moved through the entrance end of the deposition conduit and then out of the interior region through the deposition conduit as a result of the interior region of the container being pressurized by the pressure source.

25. The device of claim 24, wherein the separator apparatus comprises a liquid chromatography apparatus.

26. The device of claim 24, wherein the separator apparatus comprises a capillary electrochromatography apparatus.

27. The device of claim 24, wherein the separator apparatus comprises a capillary electrophoresis apparatus.

28. The device of claim 24, wherein the separator apparatus comprises a stationary phase material in at least a portion of the delivery conduit and the stationary phase material is configured to promote separation of the analyte into its constituent molecules as the analyte flows through the delivery conduit.

29. The device of claim 24, wherein at least one of the delivery conduit and the deposition conduit is made from a fused silica material coated with a polyamide material.

30. The device of claim 24, wherein portions of the delivery and depositions conduits that are situated in the container are oriented vertically.

31. The device of claim 24, wherein the exit end of the delivery conduit is situated above the mixing space.

32. The device of claim 31, wherein the entrance end of the deposition conduit is situated beneath the mixing space.

33. The device of claim 24, wherein the entrance end of the deposition conduit is situated beneath the mixing space.

34. The device of claim 24, wherein the delivery conduit has a first internal passage of a first inside diameter extending therethrough, the deposition conduit has a second internal passage of a second inside diameter extending therethrough, and the first diameter is approximately four times the second diameter.

35. The device of claim 34, wherein the delivery conduit has a first outside diameter, the deposition conduit has a second outside diameter, and the first outside diameter is substantially equivalent to the second outside diameter.

36. The device of claim 24, wherein the mixing space is located beneath an upper surface of the matrix material contained in the container.

37. The device of claim 24, wherein the pressure source delivers nitrogen gas to the interior region of the container to pressurize the interior region of the container.

38. The device of claim 24, wherein the main passage is oriented vertically and the at least one opening is oriented horizontally.

39. The device of claim 24, wherein the junction member is made of a material that is electrically insulative.

40. The device of claim 24, wherein the junction member is made of a material that is electrically conductive.

41. The device of claim 24, wherein the junction member comprises a cylindrical tubular member, the main passage extends axially relative to the cylindrical tubular member, and the at least one opening extends radially relative to the cylindrical tubular member.

42. The device of claim 24, wherein at least one of the first conduit and the second conduit is made from a fused silica material coated with a polyamide material.

43. A fluid treatment device comprising
 a container having an interior region,
 a junction member situated in the interior region and having a main passage,
 a first conduit having a first end in the main passage and a second end outside the interior region,
 a second conduit having a first end in the main passage and a second end outside the interior region, a mixing space being defined in the main massage between the first end of the first conduit and the first end of the second conduit, the junction member having at least one opening providing fluid communication between the interior region and the mixing space.

44. The device of claim 43, wherein the first end of the first conduit is situated above the mixing space and the first end of the second conduit is situated beneath the mixing space.

45. The device of claim 43, wherein the main passage is oriented vertically and the at least one opening is oriented horizontally.

46. The device of claim 43, wherein the junction member comprises a cylindrical tubular member, the main passage extends axially relative to the cylindrical tubular member, and the at least one opening extends radially relative to the cylindrical tubular member.

47. The device of claim 43, wherein portions of the first and second conduits that are situated in the container are oriented vertically.

48. A fluid treatment method comprising the steps of:
 applying an electrical potential to electrically charge an electrically conductive first fluid contained in a first container;
 moving the electrically charged first fluid through a first conduit to a second container that contains an electrically conductive second fluid which is coupled electrically to ground;
 creating in the second container a mixture of the first and second fluids in a mixing space defined between the first conduit and a second conduit, the mixing space being provided in a junction member that is situated in the second container and that is coupled to end of the first and second conduits; and
 transporting the mixture from the mixing space, through the second conduit, and out of the second container.

49. The method of claim 48, wherein the moving step comprises moving the electrically charged first fluid across a stationary phase material that is configured to promote separation of the first fluid into its constituent molecules.

50. The method of claim 48, further comprising the step of pressurizing the first container.

51. The method of claim 48, further comprising the step of pressurizing the second container.

52. A fluid treatment device comprising
 a first container containing a first fluid that is electrically conductive,
 a first electrode in the first fluid,
 a power supply configured to apply an electrical potential to the first electrode,
 a second container containing a second fluid that is electrically conductive, the first and second containers being pressurized by at least one gas,
 a conduit through which the first fluid moves from the first container to the second container to mix with the second fluid to form an effluent mixture,
 a second electrode in the second fluid, the second electrode being coupled to ground, and
 a second conduit through which the effluent mixture moves out of the second container to be deposited on a substrate, an electrical pathway being defined by the power supply, the first electrode, the first fluid, and the second fluid, and the second conduit and the substrate being excluded from the electrical pathway.

* * * * *

UNITED STATES PATENT AND TRADEMARK OFFICE
CERTIFICATE OF CORRECTION

PATENT NO. : 6,881,588 B2
DATED : April 19, 2005
INVENTOR(S) : Tony J. Tegeler, Yehia Mechref and Milos V. Novotny It is certified that error appears in the above-identified patent and that said Letters Patent is hereby corrected as shown below:

Column 15,
Line 45, please replace "main massage" with -- main passage --.

Column 16,
Line 22, please replace "end" with -- ends --.

Signed and Sealed this

Fourth Day of October, 2005

JON W. DUDAS
*Director of the United States Patent and Trademark Office*